United States Patent [19]

Cannata et al.

[11] Patent Number: 4,962,223
[45] Date of Patent: Oct. 9, 1990

[54] PROCESS FOR THE SYNTHESIS OF THE LEVODOPA

[75] Inventors: Vincenzo Cannata, Borgo Nuovo Pontecchio Marconi; Giancarlo Tamerlani, Potecchio Marconi; Mauro Morotti, Marzabotto, all of Italy

[73] Assignee: Ministero dell'Universita e delle Ricerca Scientifica e Tecnologica, Rome, Italy

[21] Appl. No.: 375,131

[22] Filed: Jul. 3, 1989

[30] Foreign Application Priority Data

Jul. 12, 1988 [IT] Italy ................. 21322 A/88

[51] Int. Cl.$^5$ ........................... C07C 255/33
[52] U.S. Cl. .................. 558/408; 562/446; 558/354; 558/346
[58] Field of Search ............... 562/446; 558/354, 346, 558/408

[56] References Cited

U.S. PATENT DOCUMENTS

| | | | |
|---|---|---|---|
| 3,366,679 | 1/1968 | Reinhold et al. | 562/346 |
| 3,845,076 | 10/1976 | Tsuchihashi et al. | 562/446 |
| 3,890,379 | 6/1975 | Schwartz | 558/346 |
| 4,072,698 | 2/1978 | Hylton et al. | 558/354 |
| 4,183,865 | 1/1980 | Hohnjec et al. | 558/354 |
| 4,350,641 | 9/1982 | Degner et al. | 558/346 |

FOREIGN PATENT DOCUMENTS

| | | | |
|---|---|---|---|
| 504449 | 7/1954 | Canada | 558/346 |
| 61-275253 | 12/1986 | Japan | 562/446 |

OTHER PUBLICATIONS

Koshigoe et al., Chem. Abst., vol. 109, #54332x, (1988).
Nussim et al., Chem. Abst., vol. 102, #149784r, (1985).

*Primary Examiner*—James H. Reamer
*Attorney, Agent, or Firm*—Samuels, Gauthier & Stevens

[57] ABSTRACT

New process for the synthesis of the levodopa, L-(−)-2-amino-3-(3,4-dihydroxyphenyl)propionic acid, drug used in the treatment of the Parkinson's disease. The process consists in resolving with d-camphorsulfonic acid, or with a salt thereof, the d,l-2-amino-3-(3,4-dimethoxyphenyl)propionitrile, obtained from the 3,4-dimethoxyphenylacetaldehyde, and in the subsequent hydrolysis and demethylation, by means of concentrated solutions of haloid acids, of the d-2-amino-3-(3,4-dimethoxyphenyl)propionitrile and of salts thereof.

9 Claims, No Drawings

PROCESS FOR THE SYNTHESIS OF THE LEVODOPA

BACKGROUND OF THE INVENTION

The levodopa, chemically known also as L-(−)-2-amino-3-(3,4-dihydroxyphenyl)propionic acid or as 3,4-dihydroxyphenyl-L-alanine or as 3-hydroxy-L-thyrosine, is an aminoacid of natural origin known since long time for its pharmacological activity in the treatment of the Parkinson's disease.

Its synthesis has been described in many publications like Helv. Chem. Acta, 4, 657, (1921), starting from the 3-nitro-L-thyrosine, Chem. Pharm. Bull., 10, 693, (1962) starting from 3-(3,4-methylenedioxyphenyl)-L-alanine and Ber. 105, 1168, (1972) starting from L-thyrosine.

The synthesis of levodopa by different ways was described in many patent documents. Asymmetric chemical synthesis, enzymatic and fermentative synthesis and methods for the optical resolution of precursors of the levodopa itself were reported. In the U.S. Pat. No. 4,005,127 an asymmetric chemical synthesis is described by catalytic asymmetric hydrogenation of a racemic mixture of alfa-acetamido-4-hydroxy-3-alkoxy-cinnamic acids in presence of a stereospecific catalyst made by a coordination complex between a noble metal and an optically active phosphine or arsine.

Processes by enzymatic and fermentative way are described in the German Patent Publication No. DT-OS 2102793, by fermentation of the L-thyrosine, in the U.S. Pat. No. 3,838,008, by stereoselective hydrolysis of N-acylderivatives with *Escherichia coli acylase* and in European Patent Publication EP0189938, by reaction between protected 3,4-dihydroxyphenyl pyruvic acids and glutamic or aspartic acid in presence of aminotransferase produced by genetically modified *Escherichia coli*.

Processes for the optical resolution of precursors of the levodopa, followed by hydrolysis, are described in the Belgian Patent No. BE 743496, resolution of the d,l-N-acetyl-3-(3,4-dimethoxyphenyl)alanine with d-α-methylbenzylamine, in the German Publication No. DT-OS 1963991, resolution of the d,l-N-benzoyl-3,4-dihydroxyphenylalanine with cinchonidine, in the German publication No. DT-OS 2039253, resolution of the d,l-N-benzoyl-3,4-dimethoxyphenylalanine with D-(−)-threo-1-m-nitrophenyl-2-amino-1,3-propandiol and in the U.S. Pat. No. 4,716,246, selective crystallization of the d,l-N-acetyl-3-(4-acetoxy-3-methoxyphenyl)alanine.

The process for the synthesis of the levodopa described in the present invention is completely new and consists in the optical resolution of the d,l-2-amino-3-(3,4-dimethoxyphenyl)propionitrile with d-camphorsulfonic acid and in the subsequent hydrolysis and demethylation of the d-2-amino-3-(3,4-dimethoxyphenyl)propionitrile.

The d,l-2-amino-3-(3,4-dimethoxyphenyl)propionitrile is known from the Israeli Pat. No. IL 59048, but the method for its synthesis described in the present invention is totally different. Moreover, both its separation into the corresponding enantiomers and the hydrolysis followed by the demethylation of the d enantiomer, to obtain the desired end product, are unknown.

DESCRIPTION OF THE INVENTION

The present invention refers to a new chemical process for the production of the antiparkinsonian drug levodopa (INN), which is an aminoacid present also in the nature, chemically known as L-(−)-2-amino-3-(3,4-dihydroxyphenyl)propionic acid or as 3-hydroxy-L-tyrosine.

The process described in the present invention starts from the 3,4-dimethoxyphenylacetaldehyde of formula

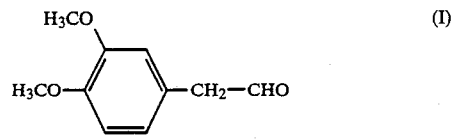

which is treated with an alkali metal cyanide in presence of ammonium chloride and of ammonium hydroxyde, to give a racemic aminonitrile of formula

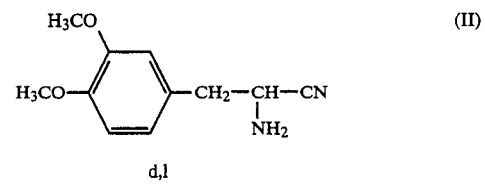

Said racemic aminonitrile, or a salt thereof like, for instance, the hydrochloride, is subjected to an optical resolution by means of d-camphorsulfonic acid, or an alkali or an earth-alkali metal salt or an ammonium salt thereof, obtaining the crystallization of the diastereoisomer salt made by the d-camphorsulfonic acid and by the d-2-amino-3-(3,4-dimethoxyphenyl)propionitrile of formula

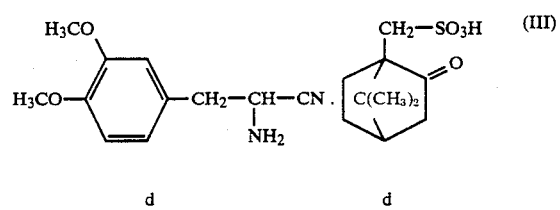

By treating said salt of formula (III) in an alkaline medium in presence of an organic solvent, the d-2-amino-3-(3,4-dimethoxyphenyl)propionitrile of formula

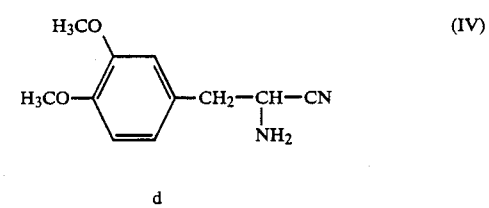

is obtained which, by treatment with an aqueous solution of hydrochloric acid and subsequent insufflation of gaseous hydrochloric acid or addition of a concentrated aqueous solution of hydrochloric acid or of an alkali metal chloride or of ammonium chloride, gives the d-2-amino-3-(3,4-dimethoxyphenyl)propionitrile hydrochloride of formula

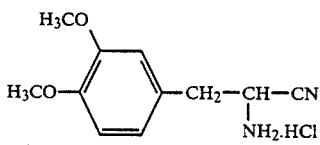

d

The compounds of formula (III), (IV) and (V) are new and therefore they constitute a further object of the present invention.

The hydrolysis and the demethylation of the compounds of formula (III), (IV) and (V) in acidic medium gives the L-(−)-2-amino-3-(3,4-dihydroxyphenyl)propionic acid or 3-hydroxy-L-thyrosine of formula

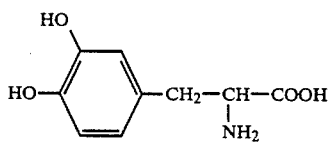

L-(−)

which corresponds to the product known as levodopa.

The acidic hydrolysis of the d-2-amino-3-(3,4-dimethoxyphenyl)propionitrile or of the salts thereof under mild conditions of temperature and of time leads to the formation of the corresponding amide of formula

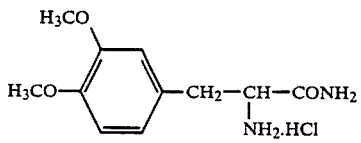

d which is new and therefore constitutes a further object of the present invention.

Also the amide of formula (VII), by boiling in acidic ambient, preferably in presence of an aqueous haloid acid, gives the desired levodopa.

According to a preferred aspect of the present invention, a molar equivalent of 3,4-dimethoxyphenylacetaldehyde of formula (I) is reacted with from about 1 to about 3 molar equivalents of an alkali metal cyanide, preferably sodium cyanide, and of ammonium chloride in presence of from about 3 to about 10 molar equivalents of ammonium hydroxide in aqueous solution, in presence of an organic solvent immiscible with water selected between the alkyl halides containing from 1 to 4 carbon atoms and the aromatic hydrocarbons, preferably methylene chloride. The reaction takes place at a temperature comprised between about 30° C. and about 70° C. for a period of time comprised between about 1 and about 8 hours. The racemic aminonitrile can be isolated from the reaction medium both as base and as salt. The racemic aminonitrile of formula (II) or a salt thereof is subjected to resolution by means of salification in water or in polar organic solvents or in mixtures thereof or mixtures thereof with water, with from about 0.5 to about 2 molar equivalents of d-camphorsulfonic acid or of an ammonium or an alkali metal or an alkali-earth metal salt thereof. The d-camphorsulfonic acid and its ammonium salt are the preferred resolving agents. Polar organic solvents which can be advantageously used, alone or in admixture among them or with water, are the alcohols containing from 1 to 4 carbon atoms, the alkyl amides, the acetonitrile and the dimethylsulfoxide, the methyl alcohol being the preferred one.

When the salification is carried out in water, the temperature is kept between about 35° C. and about 90° C., optionally seeding the aqueous solution with crystals of d-2-amino-3-(3,4-dimethoxyphenyl)propionitrile d-camphorsulfonate at a temperature of about 35° C. The d-2-amino-3-(3,4-dimethoxyphenyl)propionitrile d-camphorsulfonate of formula (III) crystallizes by cooling at a temperature comprised between about 15° C. and about 25° C. for a period of time comprised between about 2 and about 12 hours.

The d-2-amino-3-(3,4-dimethoxyphenyl)propionitrile of formula (IV) is obtained by treating a suspension of said salt of formula (III) in a mixture of water and of an organic solvent immiscible with water, like an aromatic hydrocarbon or an aliphatic halide containing from 1 to 4 carbon atoms, preferably methylene chloride, with a concentrated aqueous solution of ammonium hydroxide up to a pH comprised between about 5 and about 7, preferably pH 6.5. This compound is extracted in the organic solvent from which it is subsequently reextracted by means of a diluted aqueous solution of hydrochloric acid. The d-2-amino-3-(3,4-dimethoxyphenyl)propionitrile hydrochloride of formula (V) crystallizes by addition of gaseous hydrochloric acid or of a 32% (w/v) aqueous hydrochloric acid or of an alkali metal or ammonium chloride. The end reaction of hydrolysis of the aminonitrile to aminoacid and the removal of the methoxy groups is carried out by treating the d-2-amino-3-(3,4-dimethoxyphenyl)propionitrile of formula (IV) or its salts, i.e. the d-camphorsulphonate of formula (III) and the hydrochloride of formula (V), by means of concentrated aqueous solutions of haloid acids selected from hydrobromic acid, hydrochloric acid and mixtures thereof at a temperature comprised between about 40° C. and the boiling temperature of the reaction mixture for a period of time comprised from about 2 and about 12 hours. The reaction mixture is then cooled to room temperature, facultatively in presence of an inert gas, is diluted with water and is brought to pH 4.5 by addition of an aqueous solution of ammonium hydroxide or of an alkali metal hydroxide. The reaction mixture is then cooled to a temperature between about 0° C. and about 10° C. and the L-(−)-2-amino-3-(3,4-dihydroxyphenyl)propionic acid of formula (VI), corresponding to the drug internationally known as levodopa, is collected by filtration. The obtained product can be subjected to a further purification by means of an acid-base treatment, decolourization on active charcoal and filtration on dicalite.

When the transformation to levodopa is carried out on the compound of formula (IV) (d-camphorsulfonate of the d-aminonitrile), it is preferred to put the liberation of the aminonitrile of formula (III) by treatment with a concentrated aqueous solution of ammonium hydroxide up to pH 6.5 beforehand the acidic hydrolysis in order to recover the resolving agent d-camphorsulfonic acid.

The levodopa of formula (VI) can be obtained also by hydrolysis and demethylation of the amide of formula (VII) which is obtained by heating the nitrile of formula (IV) or its salts with a concentrated aqueous solution of a haloid acid, preferably hydrochloric acid, at a temperature comprised between about 40° C. and about 50° C. for a period of time comprised between about 30 minutes and about 2 hours. The so obtained amide of formula VII is then hydrolyzed and demethylated by treatment with a concentrated aqueous solution of a haloid acid, preferably hydrobromic acid, at the boiling temperature of the reaction mixture for a period of time comprised between about 4 and about 8 hours.

The desired levodopa is obtained with very high yields by treating the reaction mixture in the same manner as for the hydrolysis and the demethylation of the aminonitrile of formula (IV).

This yield remains very high also after the acid-base treatment of purification in order to obtain a very pure levodopa, in accordance with the standards of the Official Pharmacopoeias.

The hereinbelow reported examples have to be considered as a further illustration and not as a limitation of the present invention.

EXAMPLE 1 d,l-2-amino-3-(3,4-dimethoxyphenyl)propionitrile hydrochloride 63.24 Grams of 3,4-dimethoxyphenylacetaldehyde dissolved in 50 ml. of methylene chloride are added in about 30 minutes to a solution made by 110 ml of water, 220 ml of a 27% (w/v) aqueous solution of ammonium hydroxide, 20.9 g of sodium cyanide and 35.5 g of ammonium chloride, while keeping the temperature at about 40° C. The reaction mixture is kept between 45° C. and 50° C. for two hours and the two phases are separated after cooling to 25° C. The aqueous phase is twice extracted with 100 ml of methylene chloride and then is discarded while the organic phase, containing the nitrile, is extracted with a mixture of 270 ml of water and of 37 ml of 37% (w/v) aqueous hydrochloric acid. The aqueous solution containing the aminonitrile hydrochloride is kept under stirring for 12 hours and in this way the product crystallizes. The suspension is then saturated with gaseous hydrochloric acid, kept under stirring for two hours at room temperature and for other two hours at 10° C. and then is filtered. The nitrile hydrochloride is dried under vacuum and shows m.p.=191° C. with decomposition. 67 Grams of product are obtained with a yield of 78.6%.

EXAMPLE 2 d,l-2-amino-3-(3,4-dimethoxyphenyl)propionitrile

A mixture of 24.3 g of d,l-2-amino-3-(3,4-dimethoxyphenyl)propionitrile hydrochloride, 100 ml of water and 10 ml of toluene is brought to pH 6.5 by addition of a 27% (w/v) aqueous solution of ammonium hydroxide under stirring while lowering the temperature up to 0° C. The precipitate is filtered, washed on the filter first with cold water and then with petroleum ether and dried under vacuum obtaining 18.1 g of product with a yield of 88%. The product has m.p.=65° C.–66° C.

EXAMPLE 3 d-2-amino-3-(3,4-dimethoxyphenyl)propionitrile d-camphorsulfonate 24.93 Grams of the ammonium salt of the d-camphorsulfonic acid and 24.28 g of d,l-2-amino-3-(3,4-dimethoxyphenyl)propionitrile hydrochloride are dissolved in 120 ml of water containing 1 ml of 32% (w/v) aqueous hydrochloride acid. The mixture is heated to 35° C. and is seeded with d-2-amino-3-(3,4-dimethoxyphenyl)propionitrile d-camphorsulfonate. The reaction mixture is kept one night under stirring while keeping the temperature at 25° C., then it is filtered and the obtained solid is washed with 15 ml of ethyl alcohol and dried under vacuum at 40° C. 15.7 Grams of product having $[\alpha]_A^{20} = +29.7°$ (c=1% in methyl alcohol) and m.p.=178° C. with decomposition, are obtained with a yield of 76% calculated over the isomer d present in the racemic mixture of the d,l-nitrile.

EXAMPLE 4 d-2-amino-3-(3,4-dimethoxyphenyl)propionitrile d-camphorsulfonate

A mixture of 20.62 g of d,l-2-amino-3-(3,4-dimethoxyphenyl)propionitrile and of 37.5 g of d-camphorsulfonic acid monohydrate in 150 ml of water is heated at a temperature of about 70° C. up to complete dissolution. The solution is then cooled to 35° C. and is seeded with d-2-amino-3-(3,4-dimethoxyphenyl)propionitrile d-camphorsulfonate. The reaction mixture is kept at 25° C. for 3 hours and then is filtered. The obtained solid is washed with 20 ml of ethyl alcohol and dried in oven under vacuum at about 40° C. 28.1 Grams of product having $[\alpha]_A^{20} = +29.5°$ (c=1% in methyl alcohol) are obtained with a yield of 78% calculated as in example 3.

EXAMPLE 5 d-2-amino-3-(3,4-dimethoxyphenyl)propionitrile d-camphorsulfonate 10.3 Grams of d,l-2-amino-3-(3,4-dimethoxyphenyl)propionitrile are dissolved in a solution containing 13.75 g of d-camphorsulfonic acid monohydrate in 60 ml. of methyl alcohol and the crystallization is seeded by adding d-2-amino-3-(3,4-dimethoxyphenyl)propionitrile d-camphorsulfonate. The reaction mixture is kept 2 hours under stirring at room temperature and then is kept standing at 20° C. for 12 hours. After filtration, washing with little ethyl alcohol and drying, 8.5 g of product are obtained, having $[\alpha]_A^{20} = +26.5°$, with a yield of 77% calculated as in example 3. A sample of product is further purified by crystallization from methyl alcohol obtaining a pure product having $[\alpha]_A^{20} = +29.5°$.

EXAMPLE 6 d-2-amino-3-(3,4-dimethoxyphenyl)propionitrile 43.85 Grams of d-2-amino-3-(3,4-dimethoxyphenyl)propionitrile d-camphorsulfonate are suspended in a mixture of 100 ml of water and 100 ml of methylene chloride and the pH is brought to 6.5 by adding a concentrated aqueous solution of ammonium hydroxide. The phases are separated, the aqueous phase is discarded while the organic phase is made anhydrous on anhydrous sodium sulfate, decolourized on active charcoal, filtered on dicalite and then evaporated to dryness under vacuum. The residue is treated with toluene, partially evaporated under vacuum and, after cooling, the solid is filtered, washed on the filter with little toluene and petroleum ether and dried under vacuum. 18.3 Grams of product with a yield of 88% are obtained. The product has m.p.=83° C.–84° C. and $[\alpha]_A^{20} = +17°$ (c=1% in methyl alcohol).

EXAMPLE 7

L-(−)-2-amino-3-(3,4-dihydroxyphenyl)propionic acid

100 Grams of d-2-amino-3-(3,4-dimethoxyphenyl)propionitrile d-camphorsulfonate are suspended in a mixture of 250 ml of water and 100 ml of methylene chloride and the pH is brought to 6.5 by adding a 27% (w/v) aqueous solution of ammonium hydroxide. The phases are separated and the aqueous phase is extracted three times with 50 ml of methylene chloride and then it is discarded. The organic phases are collected and slowly added to 200 ml of a 48% (w/v) aqueous solution of hydrobromic acid while keeping the temperature at about 50° C. and distilling off the methylene chloride. At the end of the addition, the temperature is kept at about 90° C. for 3 hours distilling off the remaining methylene chloride and then eliminating the distillate until the boiling temperature of the reaction mixture reaches 118° C. The reaction mixture is kept at this temperature for 6 hours and then is cooled to 20° C. under nitrogen atmosphere, added with 150 ml of water and 1.5 g of decolourizing carbon and filtered on dicalite. The solution is brought to pH 4.5 by means of a 27% (w/v) aqueous solution of ammonium hydroxide keeping the temperature at about 35° C. for half an hour and then at about 10° C. for 1 hour. The obtained suspension is filtered and the solid is washed first with water and then with acetone and subsequently it is dried under vacuum.

38.8 Grams of product having $[\alpha]_A^{20} = -11.1°$ (c=1 in 1N aqueous hydrochloric acid) are obtained with a yield of 86%. 30 Grams of this product are purified by dissolving them in a mixture made of 150 ml of water and 16.8 ml of a 32% aqueous solution of hydrochloric acid. The solution is treated with 1 g of decolourizing carbon and filtered on dicalite. 1 Gram of ascorbic acid and 2 ml of a 27% (w/v) aqueous solution of ammonium hydroxide are then added to the solution which is slowly brought to pH 4.5 under nitrogen atmosphere by addition of a 27% (w/v) aqueous solution of ammonium hydroxide, while keeping the temperature at about 60° C. After cooling to 5° C., the product is filtered, washed on the filter first with cold water and then with acetone and dried at 40° C. under vacuum. 27.8 Grams of pure product are obtained having $[\alpha]_A^{20} = -12.9°$ (c=5.12% in 1N aqueous hydrochloric acid). The purification yield is equal to 92.7% while the overall end yield is equal to 79.7%.

EXAMPLE 8 d-2-amino-3-(3,4-dimethoxyphenyl)propionitrile hydrochloride

23 Grams of d-2-amino-3-(3,4-dimethoxyphenyl)propionitrile d-camphorsulfonate are suspended in a mixture of 60 ml of water and of 60 ml of methylene chloride and the pH value is brought to 6.5 by addition of a concentrated aqueous solution of ammonium hydroxide. The two phases are separated, the aqueous phase is extracted with 30 ml of methylene chloride and then is discarded while the organic phases are collected, washed with 20 ml of water and then the nitrile is extracted by means of a mixture made by 40 ml of water and 6 ml of 32% (w/v) aqueous hydrochloric acid. The d-2-amino-3-(3,4-dimethoxyphenyl)propionitrile hydrochloride is precipitated by addition of 40 ml of 32% (w/v) aqueous hydrochloric acid. The suspension is cooled to 4° C. and is filtered. The precipitate is washed on the filter with acetone and dried under vacuum obtaining 11 g of product with a yield of 86%. The product has m.p.=183° C. with decomposition and $[\alpha]_A^{20} = +11.9°$ (c=1% in methyl alcohol).

EXAMPLE 9

L-(−)-2-amino-3-(3,4-dihydroxyphenyl)propanoic acid

A mixture of 9 g of d-2-amino-3-(3,4-dimethoxyphenyl)propionitrile hydrochloride and of 40 ml of 48% (W/V) aqueous hydrobromic acid is heated at the boiling temperature for 6 hours and then is concentrated to a small volume by evaporation under vacuum and is added with 80 ml of water. The solution is decolourized with active charcoal, filtered on dicalite and the pH is brought to 4.5 by addition of a 27% (w/v) aqueous solution of ammonium hydroxide.

By cooling to +3° C. a precipitate is obtained which is filtered, washed on the filter first with water and then with acetone and lastly is dried under vacuum at 40° C. obtaining 6 g of product with a yield of 82%.

The product has $[\alpha]_A^{20} = -12.7°$ (c=5.12% in 1N acqueous hydrochloric acid).

EXAMPLE 10

L-(−)-2-amino-3-(3,4-dihydroxyphenyl)propanoic acid

A mixture made of 10.3 g of d-2-amino-3-(3,4-dimethoxyphenyl)propionitrile and of 56 ml of a 48% (w/v) aqueous hydrobromic acid is heated to the boiling temperature for 3 hours. The reaction mixture is then cooled under nitrogen atmosphere, evaporated under vacuum to small volume, diluted with 60 ml of water, decolourized with 0.5 g of charcoal and filtered on dicalite. A 27% (w/v) aqueous solution of ammonium hydroxide is added to the filtrate under nitrogen atmosphere up to pH 4.5. The suspension is cooled to 5° C. and is filtered. The solid is washed on the filter with cold water and with acetone obtaining, after drying under vacuum, 9.2 g of levodopa having $[\alpha]_A^{20} = -12.6°$ (c=1% in 5.12N hydrochloric acid) with a yield of 93%.

EXAMPLE 11 d-2-amino-3-(3,4-dimethoxyphenyl)propionamide hydrochloride

In 100 ml of a 32% (w/v) aqueous solution of hydrochloric acid, 24.3 g of d-2-amino-3-(3,4-dimethoxyphenyl)propionitrile hydrochloride are suspended and the reaction mixture is heated at 45° C. for about 1 hour and then is cooled to 5° C. The suspension is filtered, the solid is washed on the filter with 20 ml of a 32% (w/v) cold aqueous solution of hydrochloric acid and with acetone and is dried under vacuum. 19.3 Grams of product having $[\alpha]_A^{20} = +15.7°$ (c=1% in methyl alcohol) and m.p.=251° C.−252° C. with decomposition, are obtained with a yield equal to 74%.

EXAMPLE 12

L-(−)-2-amino-3-(3,4-dihydroxyphenyl)propanoic acid

A mixture made of 26.1 g of d-2-amino-3-(3,4-dimethoxyphenyl)propionamide hydrochloride and of 45 ml of a 48% (w/v) aqueous solution of hydrobromic acid is heated to the boiling temperature while distilling off the solvent until the reaction mixture reaches the boiling temperature of 118° C. The reaction mixture is heated to this temperature, without any distillation, for another 5 hours. The reaction mixture is then cooled to 60° C.

under nitrogen atmosphere, added with 50 ml of water and the pH is brought to 4.5 by adding a 27% (w/v) aqueous solution of ammonium hydroxide. The suspension is cooled for 1 hour to 10° C. and then is filtered. The solid is washed first with cold water, then with acetone and lastly it is dried under vacuum giving 19.3 g of product having $[\alpha]_\Delta^{20} = -11.7°$ (c=5.12% in 1N hydrochloric acid), with a yield of 97%.

Said product is purified by acid-base treatment as described in example 7 giving 17.4 g of pure L-(−)-2-amino-3-(3,4-dihydroxyphenyl)propionic acid having $[\alpha]_\Delta^{20} = -13°$ (c=5.12% in 1N aqueous hydrochloric acid), with an overall end yield of 88%.

We claim:

1. Process for the synthesis of the L-(−)-2-amino-3-(3,4-dihydroxyphenyl)propanoic acid of formula

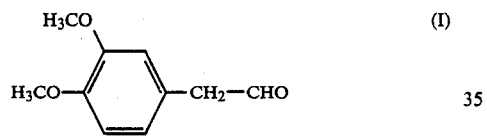

L-(−)

which comprises:

(a) reacting a molar equivalent of 3,4-dimethoxyphenylacetaldehyde of formula

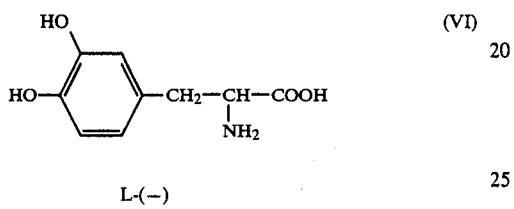

with from about 1 to about 3 molar equivalents of an alkali metal cyanide and of ammonium chloride in presence of from about 3 to about 10 molar equivalents of ammonium hydroxide in aqueous solution, in presence of an organic solvent immiscible with water selected between the alkyl halides containing from 1 to 4 carbon atoms and the aromatic hydrocarbons, at a temperature comprised between about 30° C. and about 70° C. for a period of time comprised between about 1 and about 8 hours to give the d,l-2-amino-3-(3,4-dimethoxyphenyl)propionitrile of formula

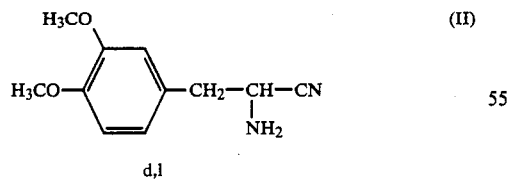

d,l (b) resolving said d,l-aminonitrile of formula (II), or a salt thereof, by salification with from about 0.5 to about 2 molar equivalents of d-camphorsulfonic acid or of an ammonium, alkali metal or alkali-earth metal salt thereof, in water or in polar organic solvents or in mixtures thereof or in mixtures thereof with water, facultatively seeding with d-2-amino-3-(3,4-dimethoxyphenyl)propionitrile d-camphorsulfonate;

(c) treating the so obtained d-2-amino-3-(3,4-dimethoxyphenyl)propionitrile d-camphorsulfonate of formula

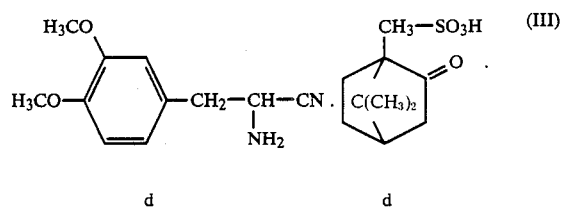

d    d with a concentrated aqueous solution of ammonium hydroxide up to about pH 6.5 to obtain d-2-amino-3-(3,4-dimethoxyphenyl)propionitrile of formula

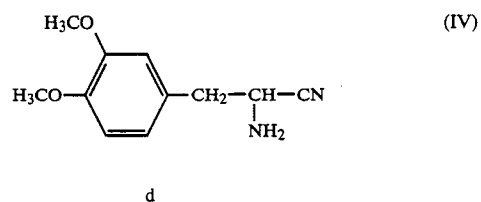

d which, by treatment with aqueous hydrochloric acid gives the d-2-amino-3-(3,4-dimethoxyphenyl)propionitrile hydrochloride of formula

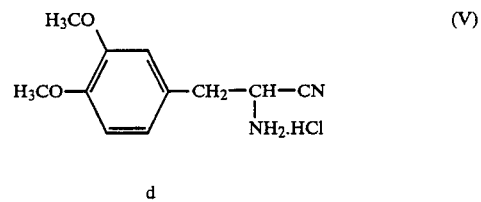

d (d) hydrolyzing and demethylating the d-2-amino-3-(3,4-dimethoxyphenyl)propionitrile of formula (IV), or its salts of formula (III) and (V), by treatment with concentrated aqueous solutions of haloid acids or of mixtures thereof at temperatures comprised between about 40° C. and the boiling temperature of the reaction mixture for a period of time comprised between about 2 and about 12 hours, to obtain, after dilution with water, addition of concentrated aqueous solution of ammonium hydroxide up to pH 4.5 and cooling to a temperature comprised between about 0° C. and about 10° C., the desired L-(−)-2-amino-3-(3,4-dihydroxyphenyl)propanoic acid of formula

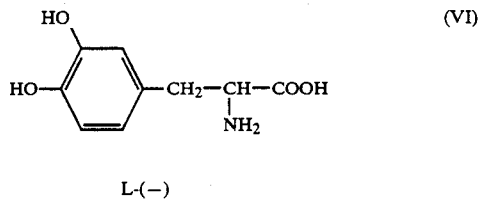

L-(−)

2. Process according to claim 1 wherein the organic solvent immiscible with water is methylene chloride.

3. Process according to claim 1 wherein the alkali metal cyanide is the sodium cyanide.

4. Process according to claim 1 wherein the resolving agents are selected between d-camphorsulfonic acid and its ammonium salt.

5. Process according to claim 1 wherein the polar organic solvents are selected from the alcohols containing from 1 to 4 carbon atoms, the alkyl amides, acetonitrile and dimethylsulfoxide.

6. Process according to claim 1 wherein the haloid acids are selected between hydrobromic acid and hydrochloric acid.

7. A process according to claim 1 wherein the hydrolysis of the d-2-amino-3-(3,4-dimethoxyphenyl)propionitrile of formula (IV), or of its salts of formula (III) and (V) is carried out with a concentrated aqueous solution of a haloid acid at a temperature comprised between about 40° C. and about 50° C. for a period of time comprised between about 0.5 and about 2 hours to give the d-2-amino-3-(3,4-dimethoxyphenyl)propionamide of formula

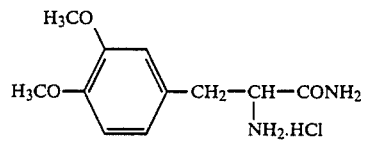

d which by treatment with a concentrated aqueous solution of a haloid acid, at the boiling temperature of the reaction mixture, for a period of time comprised between about 4 and about 8 hours gives the L-(−)-2-amino-3-(3,4-dihydroxyphenyl)propionic acid of formula (VI).

8. A product which is the d-2-amino-3-(3,4-dimethoxyphenyl)propionitrile d-camphorsulfonate.

9. Use of the compound of claim 8 in the synthesis of the L-(−)-2-amino-3-(3,4-dihydroxyphenyl)propanoic acid.

* * * * *